(12) United States Patent
Tribelhorn et al.

(10) Patent No.: US 7,674,340 B2
(45) Date of Patent: Mar. 9, 2010

(54) STABILIZER FOR ORGANIC SOLVENTS

(75) Inventors: Ulrich Tribelhorn, Ebikon (CH); Marius Kuemin, Hunenberg (CH)

(73) Assignee: Dow Global Technologies, Inc., Midland, MI (US)

( * ) Notice: Subject to any disclaimer, the term of this patent is extended or adjusted under 35 U.S.C. 154(b) by 0 days.

(21) Appl. No.: 11/995,162

(22) PCT Filed: May 1, 2006

(86) PCT No.: PCT/US2006/016768

§ 371 (c)(1),
(2), (4) Date: Jul. 8, 2008

(87) PCT Pub. No.: WO2007/011444

PCT Pub. Date: Jan. 25, 2007

(65) Prior Publication Data

US 2009/0176686 A1      Jul. 9, 2009

Related U.S. Application Data

(60) Provisional application No. 60/699,706, filed on Jul. 15, 2005.

(51) Int. Cl.
*B08B 3/04* (2006.01)
*C11D 3/30* (2006.01)
*C11D 3/43* (2006.01)

(52) U.S. Cl. .............. 134/42; 134/39; 134/40; 134/41; 510/245; 510/251; 510/264; 510/267; 510/433; 510/499

(58) Field of Classification Search ............. 510/245, 510/251, 264, 267, 433, 499; 134/39, 40, 134/41, 42
See application file for complete search history.

(56) References Cited

U.S. PATENT DOCUMENTS

| 3,424,805 A | | 1/1969 | Fruhwirth et al. | |
| 4,032,584 A | * | 6/1977 | Irani | 570/111 |
| 4,034,051 A | | 7/1977 | Dempf et al. | |
| 5,597,788 A | * | 1/1997 | Stevens | 510/212 |

FOREIGN PATENT DOCUMENTS

| EP | 1042257 | | 10/2000 |
| JP | 56-034639 | * | 4/1981 |
| WO | 0236531 | | 5/2002 |

OTHER PUBLICATIONS

K. Blum, et al., "Epoxide Free Stabiliser for Tri : Chloroethylene—Contains Amine Ethyl Acetate, Olefin and Hydroxy-free Ether", Derwent Abstract, 1982-76959E of EP59251, Sep. 8, 1982.
Okazawa Tomiya, et al., "Stabilising methyl chloroform—by adding benzylamine as auxiliary stabilizer to methyl chloroform already containing at least two stabilisers", Derwent Abstract 1981-37174D of JP 56-034639, Apr. 6, 1981.
Osaka Soda, "Stabilization of perchloroethylene—preventing decompn into phosgene etc", Abstract, AN 1973-49332U of JP 51005364B, 1973.

* cited by examiner

*Primary Examiner*—Brian P Mruk
(74) *Attorney, Agent, or Firm*—Paul D. Hayhurst

(57) ABSTRACT

A stabilizer composition comprising a) an amine and b) a compound selected from aliphatic, non-cyclic monomeric polyunsaturated hydrocarbons and terpenes is useful for stabilizing an organic solvent against degradation.

16 Claims, 1 Drawing Sheet

STABILIZER FOR ORGANIC SOLVENTS

CROSS REFERENCE TO RELATED APPLICATIONS

Figure 1:
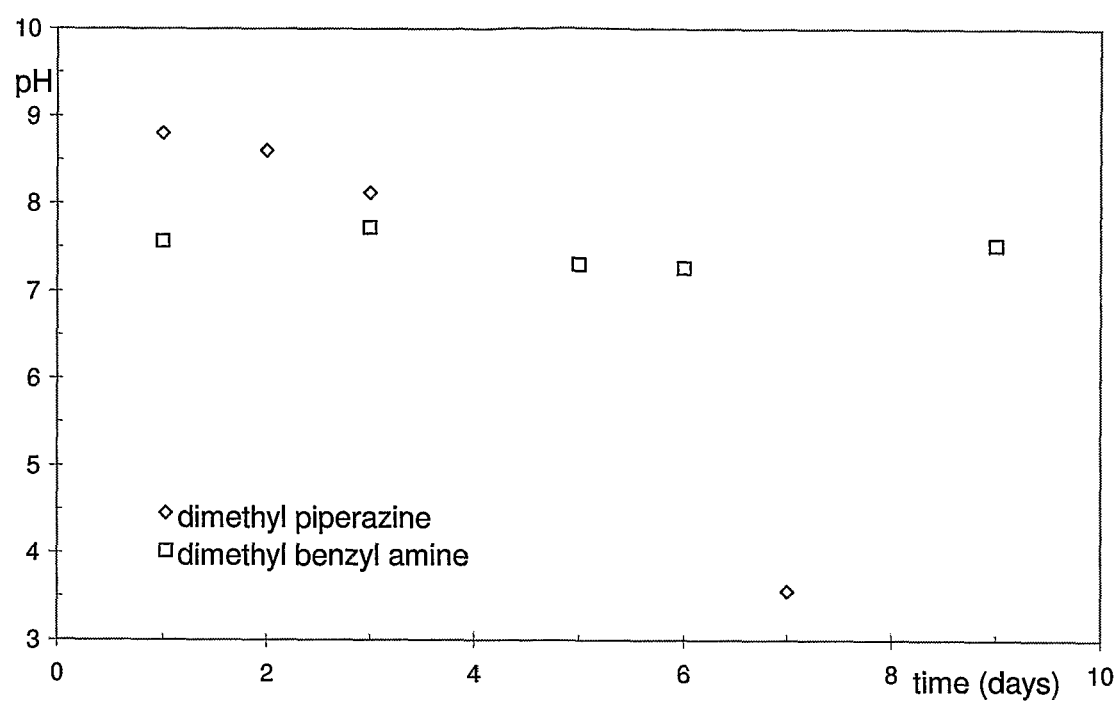

This application is a 371 of PCT/US2006/016768 filed 1 May 2006, which claims the benefit of U.S. Provisional Application Ser. No. 60/699,706, filed 15 Jul. 2005.

FIELD OF THE INVENTION

The present invention concerns a stabilizer composition and a stabilized solvent composition.

BACKGROUND OF THE INVENTION

Organic solvents, such as hydrocarbons, halogenated hydrocarbons, glycol ethers, esters or ketones, are used in several applications, such as dry-cleaning of textiles or degreasing of metals. However, it is well known that halogenated hydrocarbons, glycol ethers, esters or ketones tend to decompose when they are exposed to heat, oxygen, light or water, particularly if metals or metal salts are present. Acidic products, such as hydrochloric acid, are produced during decomposition of halogenated hydrocarbons. Therefore, it is common in the industry to add a stabilizer to halogenated hydrocarbons.

The published Patent Application WO 0236531 discloses a stabilizer composition comprising an olefinic amine with a boiling point of 5 to 80° C., an aliphatic, acyclic ester or formate of 2 to 6 carbon atoms, optionally a saturated aliphatic amine with a boiling point of 5 to 80° C. and optionally an antioxidant, such as a cyclic alkane or a pentene.

U.S. Pat. No. 3,424,805 suggests stabilization of chlorinated hydrocarbons by addition of an aliphatic diamine, triamine or polyamine. It is taught that the stabilizing effect can be increased by the addition of an aliphatic monoamine, such as diisopropylamine or pyrrole or N-alkyl pyrrole, such as N-methyl pyrrole.

European Patent No. 1 042 257 discloses a stabilizer composition for halogenated hydrocarbons which comprises an N-alkyl morpholine and a straight-chain or cyclic aliphatic amine containing no heteroatoms other than nitrogen with a boiling point of at least 150° C.

European Patent No. 0 059 251 discloses a composition for stabilizing trichloroethylene. The composition comprises an amine with a boiling point of 50 to 150° C., ethyl acetate, N-methylpyrrol and/or an alkylphenol and further diisobutylene and/or cycloheptatriene and an ether comprising no hydroxyl groups.

Typically stabilizer compositions are not added to hydrocarbons due to their well-known stability against decomposition. However it has been observed that the lack of a stabilizer often leads to an undesirable concentration of acidic compounds in the hydrocarbon which originates from the decomposition of contaminants present in the dry-cleaning of textiles or degreasing of metals and which increases over time as the hydrocarbon is recycled. The same observation has been made when using glycol ethers, esters or ketones as a solvent. The produced acidic compounds can cause corrosion problems in the cleaning operations.

Unfortunately, the stabilizer compositions suggested in the prior art often do not meet the requirements of the industry for many applications. Often the capacity of the stabilizer is reduced over time too fast which is made apparent by an increase in acidity of the organic solvent. Many stabilizers suffer in that they are not suitable for solvents of low polarity, such as hydrocarbons. Yet other stabilizers have a very high boiling point and do not stabilize the solvent when it is in the vapor phase.

Accordingly, one object of the present invention is to provide a new stabilizer composition for organic solvents. A preferred object of the present invention is to provide a stabilizer or stabilizer composition which is suitable for stabilizing an organic solvent against an undue increase in acidity over an extended period of time. Yet another preferred object of the present invention is to provide a stabilizer or stabilizer composition which is sufficiently volatile to stabilize organic solvents in the vapor phase. Yet another preferred object of the present invention is to provide a stabilizer or stabilizer composition which can not only be used in halogenated hydrocarbons but also in solvents of medium or low polarity, such as glycol ethers, esters, ketones or hydrocarbons.

SUMMARY OF THE INVENTION

One aspect of the present invention is a stabilizer composition comprising a) an amine and b) a compound selected from aliphatic, non-cyclic monomeric polyunsaturated hydrocarbons and terpenes.

Another aspect of the present invention is a solvent composition comprising a) an amine and b) a compound selected from aliphatic, non-cyclic monomeric polyunsaturated hydrocarbons and terpenes; as well as an organic solvent.

Yet another aspect of the present invention is a solvent composition comprising N,N-dimethyl benzylamine and an organic solvent.

Yet another aspect of the present invention is the use of the solvent composition above for cleaning articles.

Yet another aspect of the present invention is a method of controlling the acid content of an organic solvent, which method comprises combining the solvent with the stabilizer composition above.

Yet another aspect of the present invention is a method of controlling the acid content of an organic solvent, which method comprises combining the solvent with N,N-dimethyl benzylamine. Yet another aspect of the present invention is a method of protecting a cleaning apparatus or an article to be cleaned against corrosion while cleaning the article with an organic solvent, which method comprises incorporating in the organic solvent an effective amount of a) an amine and b) a compound selected from aliphatic, non-cyclic monomeric polyunsaturated hydrocarbons and terpenes and subjecting the article to a cleaning operation.

Yet another aspect of the present invention is a method of protecting a cleaning apparatus or an article to be cleaned against corrosion while cleaning the article with an organic solvent, which method comprises combining an effective amount of N,N-dimethyl benzylamine with the organic solvent and subjecting the article to a cleaning operation in the cleaning apparatus.

DETAILED DESCRIPTION OF THE INVENTION

Various amines a) are useful in the stabilizer composition and solvent composition of the present invention. The amine can be a primary, secondary or tertiary amine. It can be a straight-chain, branched or cyclic aliphatic amine or an aromatic amine. Preferably, the pKa of the amine a) is from 7 to 12, preferably from 7.5 to 11, more preferably from 8 to 10. The amine preferably has a boiling point of from 50 to 250° C., more preferably from 80 to 220° C., most preferably from 150 to 200° C., measured at atmospheric pressure. Preferably the solubility of the amine a) in a hydrocarbon is 5 percent or more, more preferably 10 percent or more, based on the weight of the hydrocarbon. Preferably the solubility of the amine a) in water is less than 5 percent, more preferably 2 percent or less, based on the weight of water. Tertiary amines are preferred. Exemplary of tertiary amines are saturated tertiary amines, preferably triethyl amine, diethyl n-propyl amine, ethyl di-n-propyl amine, tri-n-propyl amine, triisopropyl amine, N,N,N',N",N"-pentamethyldiethylenetriamine, N,N,N',N",N"-pentamethyl-dipropylenetriamine, N,N,N', N'-tetramethyl-1,6-hexanediamine, N,N,N',N'-tetramethyl-1,3-propanediamine, bis(2-dimethylaminoethyl)ether, bis(3-dimethylaminopropyl)amine, olefinic tertiary amines, such as allyl-dimethylamine or diallyl-methylamine; or tertiary amino alcohols, such as monoethanolamine, diethanolamine, triethanolamines, mono(iso)propanolamine, di(iso)propanolamine, tri(iso)propanolamine, N,N-dimethyl ethanolamine, N,N,-diethylethanolamine, N,N-dimethyl(iso)propanolamine and dimethylaminoethoxyethanol. More preferred amines a) comprise an aliphatic or aromatic cyclic group. The most preferred amines are triethylenediamine, N-methyl morpholine, N-ethylmorpholine, N-methyl piperidine, N-ethyl piperidine, 1,2-dimethylimidazole, 1-methylimidazole, N,N-dimethyl cyclohexyl amine, N,N-diethyl cyclohexyl amine, N-ethyl,N-methyl-cyclohexyl amine, N,N-dimethylaniline, N,N-diethylaniline, N-ethyl,N-methyl-aniline, N,N'-dimethyl-piperazine, N,N'-diethyl-piperazine, N-ethyl, N'-methyl-piperazine, N,N,-diethyl-benzylamine, N-ethyl, N-methyl-benzylamine, (N,N-dimethyl)-p-xylylamine, (N,N-dimethyl)-o-xylylamine, methyl dibenzylamine, and particularly N,N-dimethyl benzylamine. The stabilizer composition and solvent composition of the present invention also comprise a compound b) selected from aliphatic, non-cyclic monomeric polyunsaturated hydrocarbons and terpenes. By the term "aliphatic, non-cyclic monomeric polyunsaturated hydrocarbon" is meant that the hydrocarbon is aliphatic, non-cyclic, monomeric and polyunsaturated. Some of the terpenes are aliphatic, non-cyclic monomeric polyunsaturated hydrocarbons, such as 2,6-dimethyl-2,4,6-octatriene (alloocimene), but other terpenes, particularly monoterpenes, sesquiterpenes and diterpenes and the terpeneoids with oxygen-containing functional groups like alcohols, aldehydes and ketones are also useful. Preferred compounds b) are aliphatic, non-cyclic monomeric polyunsaturated hydrocarbons. The term "polyunsaturated" as used herein means that the hydrocarbon comprises at least 2, preferably from 2 to 4, most preferably 3 C=C double bonds. Compound b) is preferably a hydrocarbon comprising from 5 to 20, more preferably from 5 to 10 carbon atoms and from 2 to 4 conjugated C=C carbon double bonds. The compound b) preferably has a boiling point of from 50 to 250° C., more preferably from 80 to 220° C., most preferably from 150 to 200° C., measured at atmospheric pressure. Preferably the solubility of the monomeric hydrocarbon b) in another hydrocarbon is 5 percent or more, more preferably 10 percent or more, based on the weight of the hydrocarbon other than hydrocarbon b). Preferably the solubility of the monomeric hydrocarbon b) in water is less than 5 percent, more preferably 2 percent or less, based on the weight of water. Preferred compounds b) are 1-pentene, di-iso-butylene, α-myrcene, cis-α-ocimene and 4-trans-6-trans-alloocimene. The most preferred compound b) is 2,6-dimethyl-2,4,6-octatriene (alloocimene).

The stabilizer composition of the present invention preferably comprises from 40 to 99.9 percent, more preferably from 50 to 99 percent, most preferably from 75 to 95 percent of the amine a) and preferably from 60 to 0.1 percent, more preferably from 50 to 1 percent, most preferably from 25 to 5 percent of the component b), based on the total weight of a) and b).

The stabilizer composition or the solvent composition of the present invention may comprise one or more additional stabilizing additives c) other than compounds a) and b), such as an acid acceptor, a corrosition inhibitor, an antioxidant or a combination thereof. A preferred additional stabilizing additive c) is an epoxide, preferably isoamylene oxide, propylene oxide or, more preferably, 1,2-butylene oxide. A further stabilizing additive is an ether, preferably a dialkyl ether, such as dibutyl ether or di-sec.-butyl ether; a dialkoxymethane, such as dimethoxy methane or diethoxy methane; a glycol dialkyl ether, such as dimethoxy ethane, diethoxy ethane or butylglycol-tert.-butyl ether, a polyglycol ether, such as diglycol-tert.-butyl ether, methoxy-diglycol-tert.-butyl ether or triglycoldimethyl ether; an aryl ether, such as diphenyl ether; an aralkyl ether, an arylalkyl ether, such as anisol; or a hydroquinone dimethyl ether. Preferred antioxidants are alkyl phenols, preferably an o- and/or p-alkyl phenol which contains one or more straight-chain or branched alkyl chains comprising from 1 to 18, preferably from 2 to 8 carbon atoms, such as p-cresol, o-cresol, 2,6-dimethyl-phenol or 2,4,6-trimethyl-phenol. Preferred are p-alkyl phenols which comprise a branched $C_{3-5}$-alkyl chain, such as p-isopropyl-phenol, p-tert.-butyl phenol, 2,4-di-tert.-butyl phenol, 2,6-di-tert.-butyl-p-cresol, or amyl-phenol. Combinations of epoxides, ethers and alkyl phenols may also be used.

A preferred aspect of the present invention is a stabilizer composition which comprises an above-mentioned amine a), an above-mentioned compound b), optionally one or more additional stabilizing additives c), and optionally an organic diluent d). The organic diluent d) is preferably a hydrocarbon, a halogenated hydrocarbon, a glycol ether, an ester or a ketone described below. The diluent d) is different from the above-mentioned compounds a), b) and c). The organic diluent preferably has a boiling point above 120° C., more preferably a boiling point above 160° C. measured at atmospheric pressure. Preferred hydrocarbons are aliphatic non-cyclic or cyclic hydrocarbons other than compound b), such as isoparaffins with a boiling point above 150° C. The organic diluent preferably has about the same boiling point as the organic solvent to be stabilized. More preferably, the organic diluent is the same as the organic solvent to be stabilized. By including an organic diluent in the stabilizer composition, a stabilizer concentrate is provided which allows a user-friendly dosage and addition of the stabilizer composition to the organic solvent to be stabilized. The stabilizer composition preferably comprises 40 to 99.9 percent, more preferably from 50 to 99 percent, most preferably from 75 to 95 percent of the amine a), preferably from 60 to 0.1 percent, more preferably from 50 to 1 percent, most preferably from 25 to 5 percent of the component b), preferably from 0 to 60 percent, more preferably from 0 to 50 percent, most preferably from 0 to 25 percent of an additional stabilizing additive c), and preferably from 0 to 3000 percent, more preferably from 20 to 1000 percent, most preferably from 50 to 800 percent of the organic diluent d), all percentages being based on the total weight of a) and b). It is understood that the stabilizer composition of the present invention can comprise one or more types of amines a), compounds b), optional additional stabilizing additives c), and optional organic solvents d). However, their total amount is preferably within the weight ranges indicated above. The stabilizer composition may contain minor amounts of other components, but the sum of the components a) and b) and the optional components c) and d) preferably amounts to at least 80 percent, more preferably at least 90 percent, most preferably at least 95 percent, based on the total weight of the stabilizer composition.

The stabilizer composition of the present invention, at least in its preferred embodiments, combines many advantages. The amine a) and the compound b) have a good solubility in and a boiling point similar to the solvents listed below. This allows stabilization of the hydrocarbons and other organic solvents listed below not only in their liquid phase but also in their vapor phase. This aspect is of high importance, because even in cleaning operations using organic solvents often some water is present. For example, water can originate from the humidity in the environment or from the articles to be cleaned. Entrained water will distill azeotropically with the solvent and separate again in a condenser. Corrosion of the condenser will occur if the pH-value is below 7, especially when chloride ions are present. Moreover, the low water-solubility of the amine a) and the compound b) prevents that the stabilizer composition is washed out to a large extent in a water separator that is commonly used in cleaning processes wherein the organic solvent is recycled.

The components of the stabilizer composition of the present invention can be added individually or as a mixture to a solvent to be stabilized. According to a preferred embodiment of the present invention, an above described stabilizer concentrate is added to a solvent to be stabilized. The organic solvent preferably is a hydrocarbon different from compound b), a halogenated hydrocarbon, a glycol ether, an ester or a ketone. Preferred examples of hydrocarbons which are different from compound b) are white spirits, kerosines CAS 64742-82-1 or CAS 64742-47-8 or, more preferably an $C_9$-$C_{12}$ isoparaffin CAS 90622-57-4 or CAS 90622-58-5. Preferred halogenated hydrocarbons are $C_{1-3}$-haloalkanes or $C_{1-3}$-haloalkenes, such as n-propyl bromide, isopropyl bromide, bromomethane, chloromethane, methylene chloride, chloroform, trichloroethylene or perchloroethylene; Preferred glycol ethers are propylene glycol monomethyl ether, dipropylene glycol monomethyl ether, tripropylene glycol monomethyl ether, propylene glycol monoethyl ether, dipropylene glycol monoethyl ether, tripropylene glycol monoethyl ether, a propylene glycol monopropyl ether, a dipropylene glycol mono propylether, a tripropylene glycol monopropyl ether, a propylene glycol monobutyl ether, a dipropylene glycol monobutyl ether, propylene glycol monomethyl ether acetate, propylene glycol diacetate, dipropylene glycol dimethyl ether, diethylene glycol monomethyl ether, diethylene glycol monoethyl ether, triethylene glycol monoethyl ether, ethylene glycol monopropyl ether, ethylene glycol mono butyl ether, diethylene glycol monobutyl ether, ethylene glycol monohexyl ether, diethylene glycol monohexyl ether, ethylene glycol phenyl ether, ethylene glycol monobutyl ether acetate, diethylene glycol monobutyl ether acetate, diethylene glycol dimethyl ether and triethylene glycol dimethyl ether. The propyl groups in the listed compounds can be isopropyl or n-propyl. The butyl groups in the listed compounds can be n-butyl, isobutyl or tert-butyl. Preferred esters are n-propyl acetate, isopropyl acetate, n-propyl propionate, isopropyl propionate, n-butyl acetate, isobutyl acetate, n-butyl propionate, isobutyl propionate, n-pentyl acetate, isopentyl acetate, n-pentyl propionate and isopentyl propionate. Preferred ketones are methyl propyl ketone, methyl butyl ketone, methyl hexyl ketone, methyl heptyl ketone, diethyl ketone, ethyl propyl ketone, ethyl isopropyl ketone, ethyl butyl ketone, ethyl isobutyl ketone, ethyl pentyl ketone, ethyl isopentyl ketone, ethyl hexyl ketone, ethyl isohexyl ketone, trimethyl nonanone, cyclohexanone, trimethyl cyclohexanone and hydroxy methyl pentanone. The organic solvent preferably has a flash point above 55° C. and/or a boiling point above 150° C., measured at atmospheric pressure.

The solvent composition of the present invention preferably comprises from 5 to 20,000 ppm, more preferably from 50 to 10,000 ppm, most preferably from 100 to 5000 ppm of the amine a), preferably from 2 to 5,000 ppm, more preferably from 5 to 1000 ppm, most preferably from 20 to 500 ppm of the compound b) and, if present, preferably from 2 to 5,000 ppm, more preferably from 5 to 1000 ppm, most preferably from 20 to 500 ppm of an additional stabilizing additive c), based on the total weight of the solvent composition.

The solvent composition of the present invention is useful for cleaning articles, such as metal components in a known manner. The term "cleaning" as used herein does not only mean removal of soil but also encompasses the degreasing and drying of articles. The solvent composition of the present invention is particularly useful in the metal working industry. The solvent composition is stabilized against the build-up of acidic compounds over an extended period of time. Accordingly, the metal parts to be cleaned and the cleaning equipment do not tend to corrode to a substantial degree when treated with the solvent composition of the present invention. Furthermore, the solvent composition of the present invention can be easily regenerated by distillation and preserves the amine a) and the compound b) to a large extent.

In one of its aspects, the present invention concerns a method of controlling the acid content of an organic solvent. In another aspect, the present invention concerns a method of protecting a cleaning apparatus or an article to be cleaned against corrosion while cleaning the article with an organic solvent. Both methods comprise combining the organic solvent with an effective amount of an above-described amine a), an above-described compound b) and optionally an above-described additional stabilizing additive c), such as a known blending operation. Effective amounts of compounds a), b) and c) are described above. The article can be subjected to a cleaning operation in a cleaning apparatus in a known manner. The articles are for examples textiles or preferably metals. Preferred cleaning temperatures are from 10° C. to 200° C., more preferably from 50 C to 140° C. Preferred cleaning pressures are from 1 mbar to 1050 mbar, more preferably from 100 mbar to 1050 mbar.

While an amine a) and a compound b) in general should be used in combination to control the acid content of an organic solvent over an extended time period or to protect a cleaning apparatus or an article to be cleaned against corrosion while the article is cleaned with an organic solvent, it has surprisingly been found that N,N-dimethyl benzylamine is an excellent stabilizer even in the absence of a compound b).

Accordingly, a solvent composition which comprises N,N-dimethyl benzylamine and an organic solvent is also an aspect of the present invention. Such solvent composition preferably comprises from 5 to 20,000 ppm, more preferably from 50 to 10,000 ppm, most preferably from 100 to 5000 ppm of the N,N-dimethyl benzylamine. Alternatively, the solvent composition can be provided in the form of a concentrate which comprises a higher amount of N,N-dimethyl benzylamine and which is diluted with an organic solvent prior to its use. The solvent composition optionally also comprises an above-described additional stabilizing additive c). If present, the amount of the additional stabilizing additive c) preferably is from 2 to 5,000 ppm, more preferably from 5 to 1000 ppm, most preferably from 20 to 500 ppm, based on the total weight of the solvent composition.

Useful organic solvents are described further above, such as halogenated hydrocarbons, esters or ketones or, preferably, glycol ethers or hydrocarbons other than aliphatic, non-cyclic monomeric polyunsaturated hydrocarbons.

The invention is illustrated by the following examples which should not be construed to limit the scope of the present invention. Unless stated otherwise all parts and percentages are given by weight.

EXAMPLES 1-7 AND COMPARATIVE EXAMPLES A-G

The used solvents are:
DOWPER MC perchloroethylene, which is commercially available from The Dow Chemical Company. It comprises a specific corrosion inhibitor that makes the perchloroethylene especially suitable for heavy duty cleaning and degreasing of highly contaminated metals in closed systems with continuous distillation. DOWPER MC perchloroethylene is used for comparative purposes in Comparative Examples A and F for its well-known high stability;
perchloroethylene without corrosion inhibitor is used in Example 6;
a blend of 80 weight percent of $C_{9-12}$-isoparaffin and 20 weight percent of propylene glycol mono n-butylether is used in Examples 1 and 2 and in Comparative Example B;
$C_{9-12}$-isoparaffin is used in Examples 3 and 7 and Comparative Example C and G;
propylene glycol mono n-butylether is used in Example 4 and in Comparative Example D; and
dipropylene glycol monomethyl ether is used in Example 5 and in Comparative Example E.

The used metal working oils are:
OEST REF 72240 and OEST REF 70041: metal working fluids which are commercially available from Georg Oest Mineralölwerke GmbH & Co KG, Freudenstadt, Germany.
Vascomill 35 Art. 2907: a metal working fluid which is commercially available from Blaser Swisslube AG, Hasle-Rüegsau, Switzerland.
Multicut Stamp 60: a non-water miscible metal working fluid which is commercially available from Zeller+ Gmelin, Germany
Castrol IP 2: is a lubricant oil which is commercially available from CASTROL, USA.

The stability of the cleaning fluid is tested by the following procedure: a solvent or solvent blend, one or more metal working oils and optionally stabilizing compounds of the kinds and amounts listed in the Tables below are weighed into a flask. The blend is heated to the boiling point and kept for 6-7 days at reflux via a condenser and a water/solvent separator. Three metal strips made of steel, aluminum and brass are exposed to the vapor phase during the whole test. The test conditions are listed in the Tables below.

Samples of the distilled organic solvent are analyzed during the test period. The pH value and the chloride ions in the organic solvent are measured upon shaking the solvent with water at a volume ratio of 1:1. The pH value of the water phase is measured using a glass electrode. The approximate concentration of chloride ions is determined using commercially available test strips. The acidity, as ppm acetic acid, and the alkalinity, as ppm NaOH, are measured in the organic solvent by titration.

In Examples 6 and 7 and Comparative Examples F and G the pH value of the water phase in the water/solvent separator is measured using a glass electrode. The concentration of chloride ions in the water phase of the water/solvent separator is measured using ion chromatography.

TABLE 1

|  | Comparative Example A | Comparative Example B | Example 1 | Example 2 |
|---|---|---|---|---|
| Component of solvent composition | | | | |
| DOWPER MC | 100 parts | — | — | — |
| 80% $C_9$-$C_{12}$ isoparaffin and 20% propylene glycol mono n-butylether | — | 100 parts | 100 parts | 100 parts |
| N,N-dimethyl benzylamine | — | — | 1000 ppm | — |
| Dimethylpiperazine | — | — | — | 1000 ppm |
| 2,6-dimethyl-2,4,6-octatriene | — | — | 100 ppm | 100 ppm |
| 2,6-di-tert.-butyl-p-cresol | — | — | 100 ppm | 100 ppm |
| Test Conditions | | | | |
| Solvent | 160 g | 160 g | 160 g | 160 g |
| Oil: OEST REF 72240 | 20 g | 20 g | 20 g | 20 g |
| Oil: OEST REF 70041 | 20 g | 20 g | 20 g | 20 g |
| Reflux temperature, °C. | 95 | 95 | 95 | 95 |
| Pressure, mbar | 320 | 100 | 100 | 100 |
| Test results, analysis of distilled solvent | | | | |
| Reflux time 1 day: | | | | |
| pH value | 8 | 5.9 | 8.0 | 8.2 |
| Chloride ions, ppm | <1 | <1 | <1 | <1 |
| Reflux time 2 days: | | | | |
| pH value | 6.8 | 5.9 | 8.0 | 8.2 |
| Chloride ions, ppm | <1 | <1 | <1 | <1 |
| Reflux time 4 days: | | | | |
| pH value | 6.8 | 5.2 | 8.0 | 8.2 |
| Chloride ions, ppm | 3 | 5 | <1 | <1 |

TABLE 1-continued

|  | Comparative Example A | Comparative Example B | Example 1 | Example 2 |
|---|---|---|---|---|
| Reflux time 6 days: | | | | |
| pH value | 6.8 | 5.0 | 8.0 | 8.2 |
| Chloride ions, ppm | 5 | 5 | 3 | 5 |
| Distillation of sump after 7 days, pH | 6.8 | 4.5 | 6.8 | 8.0 |

TABLE 2

|  | Comp. Example C | Example 3 | Comp. Example D | Example 4 | Comp. Example E | Example 5 |
|---|---|---|---|---|---|---|
| Component of solvent composition | | | | | | |
| $C_9$-$C_{12}$ isoparaffin | 100 parts | 100 parts | — | — | — | — |
| propylene glycol mono n-butylether | — | — | 100 parts | 100 parts | — | — |
| dipropylene glycol monomethyl ether | — | — | — | — | 100 parts | 100 parts |
| N,N-dimethyl benzylamine | — | 1000 ppm | — | 1000 ppm | — | 1000 ppm |
| 2,6-dimethyl-2,4,6-octatriene | — | 100 ppm | — | 100 ppm | — | 100 ppm |
| 2,6-di-tert.-butyl-p-cresol | — | 100 ppm | — | 100 ppm | — | 100 ppm |
| Test Conditions | | | | | | |
| Solvent | 160 g | 160 g | 160 g | 160 g | 160 g | 160 g |
| Oil: Vascomill 35 Art. 2907 | 20 g | 20 g | 20 g | 20 g | 20 g | 20 g |
| Reflux temperature, ° C. | 95 | 95 | 95 | 95 | 95 | 95 |
| Pressure, mbar | 100 | 100 | 90 | 90 | 100 | 100 |
| Test results, analysis of distilled solvent | | | | | | |
| Reflux time 1 day: | | | | | | |
| pH value | 7 | 8.4 | 6.9 | 8.5 | 7.2 | 9.6 |
| Chloride ions, ppm | <1 | <1 | <1 | <1 | about 30 | about 30 |
| Acidity, as ppm acetic acid | — | — | 0 | — | 0 | — |
| Alkalinity, as ppm NaOH | — | 455 | — | 310 | — | 493 |
| Reflux time 2 days: | | | | | | |
| pH value | 7.3 | 8.4 | — | — | — | — |
| Chloride ions, ppm | <1 | <1 | — | — | — | — |
| Acidity, as ppm acetic acid | — | — | — | — | — | — |
| Alkalinity, as ppm NaOH | — | 437 | — | — | — | — |
| Reflux time 3 days: | | | | | | |
| pH value | — | — | — | — | 6.5 | 9.4 |
| Chloride ions, ppm | — | — | — | — | about 30 | about 30 |
| Acidity, as ppm acetic acid | — | — | — | — | 12 | — |
| Alkalinity, as ppm NaOH | — | — | — | — | — | 440 |
| Reflux time 4 days: | | | | | | |
| pH value | 7.3 | 7.9 | 6.9 | 8.4 | — | — |
| Chloride ions, ppm | <1 | <1 | <1 | <1 | — | — |
| Acidity, as ppm acetic acid | — | — | 4 | — | — | — |
| Alkalinity, as ppm NaOH | — | 420 | — | 280 | — | — |
| Reflux time 6 days: | | | | | | |
| pH value | — | — | — | — | 6 | 9.4 |
| Chloride ions, ppm | — | — | — | — | about 30 | about 30 |
| Acidity, as ppm acetic acid | — | — | — | — | 15 | — |
| Alkalinity, as ppm NaOH | — | — | — | — | — | 400 |
| Reflux time 7 days: | | | | | | |
| pH value | 6.1 | 7.9 | 4.1 | 8.6 | 4.9 | 9.6 |
| Chloride ions, ppm | <1 | <1 | <1 | <1 | about 30 | about 30 |
| Acidity, as ppm acetic acid | 10 | — | 16 | — | 18 | — |
| Alkalinity, as ppm NaOH | — | 358 | — | 280 | — | 400 |
| Distillation of sump after 7 days, pH | 6.2 | 8.0 | 7.0 | 8.0 | 5.0 | 7.0 |

The comparison between the Examples and the corresponding Comparative Examples with the same solvent illustrate the effectiveness of the stabilizer composition of the present invention for controlling the acid content in an organic solvent. The non-stabilized solvents of the Comparative Examples show a significant increase in acidity upon reflux of the solvent composition for several days, whereas the stabilized solvents in the Examples remain alkaline.

TABLE 3

| | Comparative Example F | Example 6 |
|---|---|---|
| Component of solvent composition | | |
| DOWPER MC | 100 parts | — |
| Perchloroethylene | — | 100 parts |
| N,N-dimethyl benzylamine | — | 1000 ppm |
| 2,6-dimethyl-2,4,6-octatriene | — | 100 ppm |
| 2,6-di-tert.-butyl-p-cresol | — | 100 ppm |
| Test Conditions | | |
| Solvent | 160 g | 160 g |
| Oil: Vascomill 35 Art. 2907 | 40 g | 40 g |
| Water in water/solvent separator | 20 g | 20 g |
| Reflux temperature, ° C. | 120 | 120 |
| Pressure, mbar | 980 | 980 |
| Test results, analysis of distilled solvent and of water in water/solvent separator | | |
| Reflux time 1 day: | | |
| a) analysis of solvent (distillate) | | |
| Alkalinity, as ppm NaOH | 5 | >40 |
| pH value | 8 | 8 |
| b) analysis of water in separator | | |
| pH value | 8 | 8 |
| Chloride ions, ppm | 1.5 | 3.6 |
| Reflux time 3 days: | | |
| a) analysis of solvent (distillate) | | |
| Alkalinity, as ppm NaOH | 0 | 31 |
| pH value | 7 | 8 |
| b) analysis of water in separator | | |
| pH value | 5.3 | 7 |
| Chloride ions, ppm | 118 | 21 |
| Reflux time 7 days: | | |
| a) analysis of solvent (distillate) | | |
| Alkalinity, as ppm NaOH | 0 | 15 |
| pH value | 7 | 8 |
| b) analysis of water in separator | | |
| pH value | 2 | 6.5 |
| Chloride ions, ppm | 1998 | 142 |
| Distillation of sump after 7 days, pH | 6.7 | 8.1 |

The comparison between Comparative Example F and Example 6 illustrates the higher stability of perchloroethylene that is stabilized with the stabilizer composition of the present invention over DOWPER MC perchloroethylene that is well-known and frequently used because of its high stability. The superiority of the stabilized solvent composition of the present invention is particularly evident upon analysis of the water phase in the solvent/water separator. When using the stabilized solvent composition of the present invention the pH of the water phase in the solvent/water separator is much more stable and there is a much lower build-up of chloride ions in the water phase than when using a known stabilized solvent composition. Corrosion of the solvent/water separator can be effectively prevented or minimized with the solvent composition of the present invention.

TABLE 4

| | Example 7 | Comp. Example G |
|---|---|---|
| Components of solvent composition | | |
| $C_9$-$C_{12}$ isoparaffine (percent) | 99.9 | 99.9 |
| N,N-dimethyl benzylamine (ppm) | 1000 | — |
| N,N'-dimethyl-piperazine (ppm) | — | 1000 |
| Test Conditions | | |
| Solvent (g) | 90 | 90 |
| Oil: Multicut Stamp 60 (g) | 20 | 20 |
| Oil: Castrol IP 2 (g) | 20 | 20 |
| Water in water/solvent separator (g) | 25 | 25 |
| Bath temperature (° C.) | 153 | 153 |
| Distillation bottom temperature (° C.) | 116 | 116 |
| Pressure (mbar) | 100 | 100 |

A reflux test using a water separator for solvents lighter than water is carried out in Example 7 and Comparative Example G. For determination of water phase pH and alkalinity, a 20 ml sample is taken from the water phase. Subsequent addition of 20 ml of distilled water keeps a constant phase ratio in the system. The results are shown in the attached FIGURE. The results in the FIGURE show the surprising finding that even when N,N-dimethyl benzylamine is added for stabilizing an organic solvent in the absence of a compound b), specifically for controlling its acid content, N,N-dimethyl benzylamine effectively keeps the pH in the alkaline range over an extended period of time. Other amines, such as N,N'-dimethyl-piperazine, fail to provide a satisfactory stabilizing effect in the absence of a compound b) described above. In Comparative Example G the pH drops to 3.5 after one week in spite of the somewhat higher molar concentration of N,N'-dimethyl-piperazine due to its lower molar weight than N,N-dimethyl benzylamine.

What is claimed is:

1. A stabilizer composition comprising
   a) an amine comprising N,N-dimethyl benzylamine and
   b) a compound selected from aliphatic, non-cyclic monomeric polyunsaturated hydrocarbons and terpenes.

2. The stabilizer composition of claim 1 wherein the pKa value of the amine a) is from 7 to 12.

3. The stabilizer composition of claim 1 wherein the compound b) is an aliphatic, non-cyclic monomeric polyunsaturated hydrocarbon.

4. The stabilizer composition of claim 3 wherein the compound b) is a hydrocarbon comprising from 5 to 20 carbon atoms and from 2 to 4 conjugated C=C carbon double bonds.

5. The stabilizer composition of claim 4 wherein the compound b) is 2,6-dimethyl-2,4,6-octatriene.

6. The stabilizer composition of claim 1 further comprising an additional stabilizing additive c) selected from the group consisting of acid acceptors, corrosion inhibitors, antioxidants and combinations thereof other than compounds a) and b).

7. The stabilizer composition of claim 6 wherein the stabilizing additive c) is an epoxide, an ether, an alkyl phenol or a combination thereof.

8. The stabilizer composition of claim 7 wherein the stabilizing additive c) is 2,6-di-tert.-butyl-p-cresol.

9. The solvent composition of claim 1 further comprising an organic solvent.

10. The solvent composition of claim 9 wherein the solvent is a hydrocarbon different from compound b), a halogenated hydrocarbon, a glycol ether, an ester or a ketone.

11. A composition comprising an organic solvent and a stabilizer consisting of N,N-dimethyl benzylamine.

12. The solvent composition of claim 11 wherein the organic solvent is a glycol ether or a hydrocarbon other than an aliphatic, non-cyclic monomeric polyunsaturated hydrocarbon.

13. A method comprising cleaning an article by contacting the article with the solvent composition of claim 9.

14. A method of controlling the acid content of an organic solvent which method comprises combining the solvent with the stabilizer composition of claim 1.

15. A method of protecting a cleaning apparatus or an article to be cleaned against corrosion while cleaning the article with an organic solvent, which method comprises combining with the organic solvent an effective amount of a) an amine comprising N,N-dimethyl benzylamine and b) a compound selected from aliphatic, non-cyclic monomeric polyunsaturated hydrocarbons and terpenes and subjecting the article to a cleaning operation in the cleaning apparatus.

16. A method of protecting a cleaning apparatus or an article to be cleaned against corrosion while cleaning the article with the composition of claim 11, which method comprises subjecting the article to a cleaning operation in the cleaning apparatus.

* * * * *